(12) United States Patent
Manne

(10) Patent No.: US 10,682,247 B2
(45) Date of Patent: Jun. 16, 2020

(54) SYSTEMS, APPARATUS, AND METHODS FOR DELIVERING A SEQUENCE OF SCENTS FOR THE PURPOSE OF ALTERING AN INDIVIDUAL'S APPETITE

(71) Applicant: JB Scientific, LLC, New York, NY (US)

(72) Inventor: Joseph Manne, New York, NY (US)

(73) Assignee: JB SCIENTIFIC, LLC, New York, NY (US)

( * ) Notice: Subject to any disclaimer, the term of this patent is extended or adjusted under 35 U.S.C. 154(b) by 383 days.

(21) Appl. No.: 15/119,068

(22) PCT Filed: Oct. 2, 2015

(86) PCT No.: PCT/US2015/053790
§ 371 (c)(1),
(2) Date: Aug. 15, 2016

(87) PCT Pub. No.: WO2016/057336
PCT Pub. Date: Apr. 14, 2016

(65) Prior Publication Data
US 2017/0049597 A1 Feb. 23, 2017

Related U.S. Application Data

(60) Provisional application No. 62/060,157, filed on Oct. 6, 2014.

(51) Int. Cl.
*A61F 5/00* (2006.01)
*A61L 9/12* (2006.01)
*A61L 9/04* (2006.01)

(52) U.S. Cl.
CPC .............. *A61F 5/0003* (2013.01); *A61L 9/04* (2013.01); *A61L 9/12* (2013.01); *A61L 9/125* (2013.01); *A61L 2209/111* (2013.01)

(58) Field of Classification Search
None
See application file for complete search history.

(56) References Cited

U.S. PATENT DOCUMENTS 4,582,492 A * 4/1986 Etter ...................... G09B 19/00
131/270
5,023,020 A 6/1991 Hiroji Machida et al.
(Continued)

FOREIGN PATENT DOCUMENTS

WO WO 2011059171 A2 * 5/2011 ........... A23L 33/105
WO 2013144836 A2 10/2013
(Continued)

OTHER PUBLICATIONS

International Search Report dated Dec. 28, 2015 for PCT/US2015/053790.
(Continued)

*Primary Examiner* — Eddy Saint-Vil
*Assistant Examiner* — William D Ermlick
(74) *Attorney, Agent, or Firm* — Lucas & Mercanti, LLP

(57) ABSTRACT

A plurality of scents that produce a particular effect on an individual's appetite are identified. The plurality of scents are delivered to produce the particular effect on the individual's appetite. The particular effect may include one of suppression of the individual's appetite and enhancement of the individual's appetite. Identifying a plurality of scents that produce a particular effect on an individual's appetite may include delivering a second plurality of scents to the individual, detecting a response of the individual to each respective one of the second plurality of scents, and identifying the plurality of scents that produce the particular effect on the individual's appetite based on the responses detected. A schedule for delivery of scents may be generated based on data relating to the individual's responses, and the
(Continued)

plurality of scents may be delivered in accordance with the schedule.

4 Claims, 10 Drawing Sheets

(56) References Cited

U.S. PATENT DOCUMENTS

| | | | | |
|---|---|---|---|---|
| 5,908,301 A * | 6/1999 | Lutz | ............ | G09B 5/02 |
| | | | | 128/921 |
| 6,063,028 A * | 5/2000 | Luciano | ............ | G16H 50/50 |
| | | | | 600/300 |
| 6,120,440 A * | 9/2000 | Goknar | ............ | A61B 10/00 |
| | | | | 128/923 |
| 6,663,571 B1 | 12/2003 | Njemanze | | |
| 6,803,987 B2 | 10/2004 | Manne | | |
| 7,389,943 B2 | 6/2008 | Jaworski | | |
| 7,469,844 B2 | 12/2008 | Conway et al. | | |
| 7,484,716 B2 | 2/2009 | Ford Morie et al. | | |
| 7,622,073 B2 | 11/2009 | Schramm et al. | | |
| 7,820,208 B2 * | 10/2010 | Hirsch | ............ | A23L 33/20 |
| | | | | 424/725 |
| 8,196,902 B1 | 6/2012 | Pystin | | |
| 8,877,139 B2 * | 11/2014 | Diersing | ............ | A61L 9/01 |
| | | | | 239/34 |
| 9,357,865 B2 * | 6/2016 | Baym | ............ | A47G 21/02 |
| 9,446,162 B2 * | 9/2016 | Chandler | ............ | A61L 9/035 |
| 2001/0049471 A1 * | 12/2001 | Suzuki | ............ | A61B 5/0002 |
| | | | | 600/300 |
| 2002/0189608 A1 * | 12/2002 | Raudenbush | ............ | A61K 31/045 |
| | | | | 128/200.14 |
| 2004/0023197 A1 * | 2/2004 | Abraham-Fuchs | ............ | |
| | | | | G06F 19/3481 |
| | | | | 434/236 |
| 2004/0092809 A1 * | 5/2004 | DeCharms | ............ | G01R 33/4806 |
| | | | | 600/410 |
| 2006/0014124 A1 * | 1/2006 | Manu | ............ | G09B 19/0092 |
| | | | | 434/236 |
| 2006/0064037 A1 * | 3/2006 | Shalon | ............ | A61B 5/0006 |
| | | | | 600/586 |
| 2006/0251541 A1 | 11/2006 | Santandrea | | |
| 2006/0266371 A1 * | 11/2006 | Vainshelboim | ............ | A61B 5/4854 |
| | | | | 128/898 |
| 2006/0293838 A1 * | 12/2006 | Yamamoto | ............ | G01C 21/20 |
| | | | | 701/532 |
| 2007/0167348 A1 * | 7/2007 | Hirsch | ............ | C11B 9/00 |
| | | | | 512/1 |
| 2007/0248542 A1 * | 10/2007 | Kane | ............ | A61K 49/0004 |
| | | | | 424/9.1 |
| 2008/0092896 A1 * | 4/2008 | Jackson | ............ | A61F 5/0003 |
| | | | | 128/206.11 |
| 2008/0131858 A1 | 6/2008 | Gordon | | |
| 2009/0197963 A1 * | 8/2009 | Llewellyn | ............ | A61K 31/275 |
| | | | | 514/579 |
| 2011/0218407 A1 * | 9/2011 | Haberman | ............ | G06F 19/3475 |
| | | | | 600/300 |
| 2013/0038601 A1 * | 2/2013 | Han | ............ | G06T 13/40 |
| | | | | 345/419 |
| 2015/0048178 A1 * | 2/2015 | Edwards | ............ | A61L 9/032 |
| | | | | 239/13 |
| 2015/0086951 A1 * | 3/2015 | Bulut | ............ | G06F 19/3481 |
| | | | | 434/236 |
| 2015/0086952 A1 * | 3/2015 | Tsoneva | ............ | G09B 19/0092 |
| | | | | 434/236 |
| 2015/0258560 A1 * | 9/2015 | Ashby | ............ | A63B 71/0622 |
| | | | | 239/70 |
| 2015/0352062 A1 * | 12/2015 | Shalon | ............ | A61K 31/137 |
| | | | | 514/654 |
| 2016/0232599 A1 * | 8/2016 | Adrian | ............ | G06Q 30/02 |
| 2016/0374610 A1 * | 12/2016 | De Ruyter | ............ | A61B 5/486 |
| | | | | 600/301 |

FOREIGN PATENT DOCUMENTS

| | | |
|---|---|---|
| WO | 2013144917 A2 | 10/2013 |
| WO | 2014144690 A2 | 9/2014 |
| WO | 2014152594 A1 | 9/2014 |

OTHER PUBLICATIONS

Written Opinion dated Dec. 28, 2015 for PCT/US2015/053790.
IPRP dated Dec. 28, 2015 from corresponding PCT/US2015/053790.
Extended European Search Report dated May 15, 2018 from the corresponding European Application No. 15849255.6.

* cited by examiner

|  | Scent Identifier | Quantity Delivered | Observed Effect on Appetite | Duration (minutes) |
|---|---|---|---|---|
| 311 | 1 | Q-1 | -60% | 120 |
| 313 | 2 | Q-2 | 0 | 0 |
| 315 | 3 | Q-3 | +20% | 30 |
| 317 | 4 | Q-4 | -50% | 45 |
| 319 | 5 | Q-5 | -80% | 30 |

Columns: 302 (Scent Identifier), 304 (Quantity Delivered), 306 (Observed Effect on Appetite), 308 (Duration (minutes)). Table 300.

FIG. 3A

| | 391 | 392 | 393 |
|---|---|---|---|
| | Scent Identifier | Quantity | Duration |
| 396 | 1 | Q-1 | 120 minutes |
| 397 | 4 | Q-4 | 45 minutes |
| 398 | 5 | Q-5 | 30 minutes |

SYSTEMS, APPARATUS, AND METHODS FOR DELIVERING A SEQUENCE OF SCENTS FOR THE PURPOSE OF ALTERING AN INDIVIDUAL'S APPETITE

CROSS REFERENCE TO RELATED APPLICATION

This Application is a 371 of PCT/US2015/053790 filed on Oct. 2, 2015, which claims the benefit of U.S. Provisional Patent Application No. 62/060,157, filed on Oct. 6, 2014, both applications are incorporated herein in their entirety by reference.

FIELD OF THE INVENTION

This invention relates generally to systems and methods for delivering a plurality of scents to generate a response from an individual, and more specifically to systems and methods for delivering a sequence of scents to alter an individual's appetite.

BACKGROUND

It is know that flavor is conferred by two different sensory organs: the tongue and the nose. In order to experience the flavor of a food or beverage two processes must occur: olfaction and gustation. Gustation provides for a limited amount of information: sweet, sour, salty, bitter and umami. The rest of flavor is actually conferred by olfaction. Therefor olfaction plays an enormous role in one's ability to taste. Of course this is well known to anyone who has experienced nasal congestion from a cold. It becomes extremely difficult to taste one's food. The process of olfaction of food requires processes taking place on the back of the tongue, the nasopharynx and the olfactory bulb. As food or a beverage is chewed and heated inside the mouth, various aromatic compounds enter the vapor phase these rise up through the nasopharynx and stimulate receptors of the olfactory nerve. This provides an important component of flavor. It is well established that diminished olfaction can lead to decreased appetite and food intake.

The use of one or more scents to influence an individual's appetite is also established. For example, the use of a sequence of scents to suppress appetite is known; see for example, U.S. Pat. Nos. 6,803,987; and 5,023,020.

The sequential administration of inhalants is known, see for example, U.S. Pat. Nos. 8,196,902; 7,622,073; 7,484,716; 7,469,844; and 7,389,943.

Scents uniquely designed for an individual person are known, see for example, U.S. Patent Publication No. 2008/0131858; 2007/0167348, and U.S. Pat. Nos. 7,820,208; and 6,663,571.

SUMMARY

Systems, apparatus, and methods for delivering a sequence of scents for the purpose of altering an individual's appetite are provided. In accordance with one embodiment, a method of delivering a plurality of scents to influence an individual's appetite is provided. A plurality of scents that produce a particular effect on an individual's appetite are identified. The plurality of scents are delivered to produce the particular effect on the individual's appetite.

In various embodiments, the particular effects may include suppression of the individual's appetite or enhancement of the individual's appetite.

In another embodiment, identifying a plurality of scents that produce a particular effect on an individual's appetite further comprises delivering a second plurality of scents to the individual, detecting a response of the individual to each respective one of the second plurality of scents, and identifying the plurality of scents that produce the particular effect on the individual's appetite based on the responses detected.

In another embodiment, for each respective one of the second plurality of scents, a measure of the response of the individual to the respective scent is determined. The measure of the response of the individual to the respective scent may comprise, for example, a reported measure of a respective scent's effect on the individual's appetite, a measure of a duration of the response of the individual to the respective scent, etc.

In another embodiment, data relating to the responses of the individual to the second plurality of scents is stored. A schedule for delivery of scents may be generated based on the stored data. The scents may be delivered in accordance with the schedule. A scent delivery schedule may be created based on the time of day and the user's regular schedule of mealtimes, for example.

In another embodiment, a measurement of a relationship between a consumption of food by the individual while the individual is exposed to the particular scent, and time, is generated. A duration of an effectiveness of the particular scent is determined based on the measurement, and a schedule for delivery of scents is generated based on the duration.

In one embodiment, the particular effect comprises suppression of the individual's appetite. For each one of the second plurality of scents, a measure of a capacity of the respective scent to suppress the individual's appetite is determined. A plurality of scents that cause suppression of the individual's appetite are identified based on the measured capacity of each respective scent to suppress the individual's appetite.

In accordance with another embodiment, an apparatus comprises a scent storage adapted to store a first plurality of scents, a scent delivery device adapted to deliver one or more of the first plurality of scents, and a data storage adapted to store data. The apparatus also comprises a processor adapted to identify a second plurality of scents that produce a particular effect on an individual's appetite, store data identifying the second plurality of scents, and cause the scent delivery device to deliver the second plurality of scents to the individual to produce the particular effect on the individual's appetite.

In one embodiment, the processor is further adapted to generate a schedule for delivery of scents based on the data.

In another embodiment, the processor is further adapted to cause the scent delivery device to deliver the second plurality of scents to the individual in accordance with the schedule.

In another embodiment, the processor is further adapted to identify a second plurality of scents that suppress the individual's appetite.

In another embodiment, the processor is further adapted to store data indicating, for each of the second plurality of scents, a duration of an effect of the scent on the individual's appetite.

In another embodiment, the processor is further adapted to identify a second plurality of scents that enhance the individual's appetite.

In another embodiment, the processor is further adapted to identify a second plurality of scents that produce a particular effect on an individual's appetite for a particular food.

These and other advantages of the present disclosure will be apparent to those of ordinary skill in the art by reference to the following Detailed Description and the accompanying drawings.

BRIEF DESCRIPTION OF THE DRAWINGS

FIG. 3A shows a database storing information relating to various scents and an individual's responses to the scents in accordance with an embodiment;

FIG. 3B shows a scent delivery schedule that may be generated in accordance with an embodiment;

DETAILED DESCRIPTION

Figure 1:
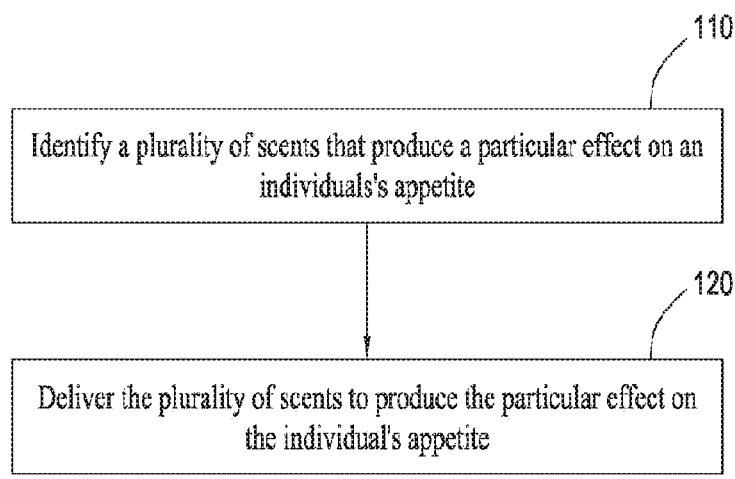
FIG. 1 is a flowchart of a method of providing a plurality of scents in order to influence an individual's appetite in accordance with an embodiment.

In accordance with various embodiments, systems, apparatus, and methods for delivering a plurality of scents to influence an individual's appetite are provided. Specifically, in accordance with one embodiment, a plurality of scents that produce a particular effect on an individual's appetite are identified. The plurality of scents are delivered to produce the particular effect on the individual's appetite. In various embodiments, the particular effect may include, for example, suppression of the individual's appetite or enhancement of the individual's appetite. A schedule for delivery of scents may be generated based on data relating to the individual's responses, and the plurality of scents may be delivered in accordance with the schedule.

There is a wide variety of available scents which have no relationship to the foods or beverages that a consumer has an undesirable craving for, and which may nevertheless have an effect on such a craving. One very obvious example is the scents which most individuals find nauseating. The smell of decomposing garbage is a good example. Creating nausea however can be unduly disruptive. There is another large class of scents which bear no relation to food. These are the floral scents. They may also be referred to as botanicals which are not related to food. For example pine fragrance is not found in food. Although pine nuts may be used in cooking they do not confer the pine scent to food. Research has shown that at the height of food craving the consumer anticipates the taste of the food they crave. By exposing the consumer to a scent unrelated to the craved food, the consumer is distracted from their anticipation and appetite for that food. Intense and uncontrolled food cravings are one of the problems experienced by dieters. Obviously, diminution of the craving does not guarantee weight loss but it may facilitate the process.

Examples of nonfood botanical scents include rose, pine, sandalwood, cedar, lavender, holly, and germanium. Obviously there are a large number of nonfood related botanical scents. There are many other nonfood associated scents including but not limited to: environmental scents (e.g. sea spray, dirt, rain etc.), industrial (e.g. new car smell, paint, smoke) and perfumes.

It is known that scents have different effects on different individuals. Everyone has experienced unique memory triggering effects of different scents. For example a child who grows up near a vegetable garden will have unique response when exposed to the familiar tomato and basil scents from his childhood. The same is true for the effect of scent on appetite. Scents do not have the same effect on each individual. That is a defect in prior attempts to use scent to inhibit appetite. The effects of scent are individually determined.

It is known from research that scents which are unrelated to the anticipated food will diminish the craving for that food. However the effect can be further optimized by choosing an individually optimized scent from the group of scents which were unrelated to the food to be consumed.

In accordance with an embodiment, an optimization process is described in which an individual's response to a group of more than one unrelated food scents is tested on the individual. The appetite suppressing response is measured for each scent and the duration of the effect is also recorded. In that way a program can be developed to present a timed sequence of different scents to the individual for a specific food or beverage craving. Furthermore a large database can be constructed with appetite suppressing responses of a large cohort of users. The data can be correlated with a large group of characteristics of the individual subjects so that more optimized scent programs can be chosen for a new user. In addition, an optimal schedule for delivering the scents may be determined for a particular individual.

In accordance with an embodiment, a method of delivering a plurality of scents to influence an individual's appetite is provided. In various embodiments, scents may be delivered to achieve a wide range of effects with respect to appetite, including suppressing the appetite in general, suppressing the appetite for a particular food, enhancing the appetite generally, enhancing the appetite for a particular food, etc.

FIG. 1 is a flowchart of a method of providing a plurality of scents in order to influence an individual's appetite in accordance with an embodiment. At step 110, a plurality of scents that produce a particular effect on an individual's appetite are identified. For example, in one embodiment, one or more scents having a suppressive effect on an individual's appetite are identified. In other embodiments, scents having other effects on an individual's appetite may be selected. At step 120, the plurality of scents are delivered to produce the particular effect on the individual's appetite. Various embodiments of the method presented in FIG. 1 are described in further detail below.

In addition to affecting an individual's appetite, scents may have the ability to affect an individual in other ways. For example, scents may affect an individual's mood. Accordingly, while systems, apparatus and methods discussed herein are described illustratively as being used to control an individual's appetite, systems, apparatus, and methods described herein may also be used to affect an individual's mood, energy level, cognitive ability, and other characteristics. For example, one or more scents affecting an individual's mood may be identified and delivered to achieve a desired effect on the individual's mood.

It is to be understood that each individual has a unique response to each respective scent, based on the individual's unique biology, the individual's unique personal history and memories, and other factors. Therefore, a practitioner typically will determine a unique set of scents for each individual.

In an illustrative embodiment, let us suppose that an individual who is overweight and who wishes to lose weight asks a practitioner to employ fragrance technology to suppress the individual's appetite generally. The practitioner accordingly identifies a series of fragrances, or scents, that effectively suppress the individual's appetite. The practitioner may be a doctor or other professional, for example.

Figure 2:
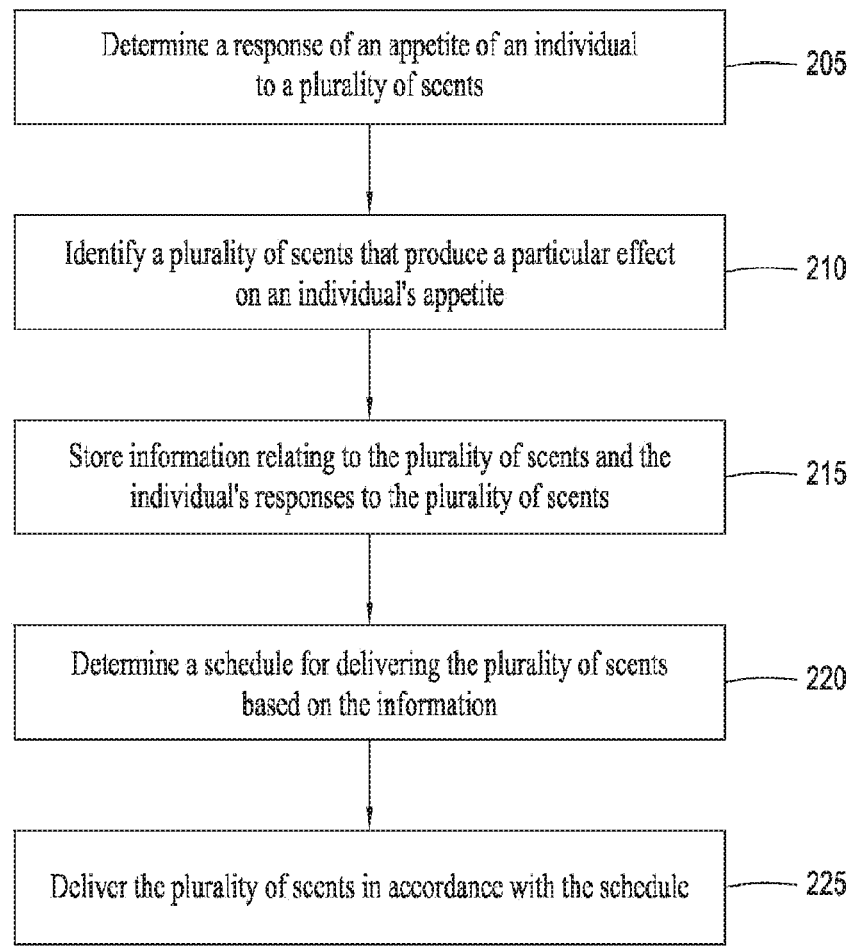
FIG. 2 shows a flowchart of a method of delivering a plurality of scents in order to alter an individual's appetite in accordance with another embodiment.

FIG. 2 shows a flowchart of a method of delivering a plurality of scents in order to alter an individual's appetite in accordance with another embodiment. At step 205, a response of an appetite of an individual to a plurality of scents is determined. In an illustrative embodiment, the practitioner may deliver to the individual a series of scents and test the individual's response to each scent. The practitioner may record various aspects of the individual's response to each scent. For example, the practitioner may measure each scent's capacity to suppress the individual's appetite. In particular, the practitioner may deliver a particular scent to the individual, and subsequently ask the individual a series of questions concerning changes in the individual's appetite; for example, the individual may be asked to grade the scent's capacity to suppress his or her appetite on a scale of one to ten. The individual's answers (including reported measures of each scent's effect on the individual's appetite) may be recorded. The practitioner may then determine a measure of the individual's response to the scent based on the individual's reported answers to the questions posed. The practitioner may also measure the duration of the individual's response to a scent. For example, the practitioner may measure how long a scent suppresses the individual's appetite. This may be accomplished by delivering a scent to the individual and then observing the individual through a period of time. The individual may be periodically asked to describe any changes in his or her appetite during the observation period. Some scents may have a relatively short effect (e.g., several minutes) while other scents may have an effect that lasts longer (e.g., several hours).

While this discussion describes several methods of measuring an effect of a scent on an individual's appetite, and several types of measures of these effects, these descriptions are not to be construed as limiting. In other embodiments, other methods, and other types of measures, may be used to obtain a measure of the effect of a scent on an individual's appetite.

In one embodiment, the practitioner may further refine the procedure by measuring each scent's capacity to suppress the individual's appetite for a particular food. For example, the individual may report experiencing a frequent craving for chocolate, and request assistance in reducing such cravings. The practitioner may accordingly deliver various scents to the individual and measure the effect of each scent on the individual's appetite for chocolate. The practitioner may record the individual's responses with respect to each delivered scent.

Referring to FIG. 2, at step 210, a plurality of scents that produce a particular effect on an individual's appetite are identified. The practitioner may test the individual's response to a variety of scents, and record the responses, in order to select a plurality of scents which have an observed capacity to suppress the individual's appetite. For example, tests may be conducted in order to identify scents which have a capacity to suppress the individual's appetite generally, or scents which have the capacity to suppress the individual's appetite for the particular food, depending on the individual's and/or the practitioner's objective.

The practitioner may also examine a plurality of scents based on knowledge or experience indicating that certain scents have a complementary effect, or even that certain scents may magnify each other's effects. Similarly, the practitioner may avoid grouping two particular scents within a plurality based on knowledge that the two scents tend to reduce each other's effectiveness. The practitioner may also access a database of previously recorded data relating to other individual's experiences/responses to various scents. Such data may assist in identifying potential candidate scents that tend to have a particular desired effect.

In the illustrative embodiment, the practitioner selects a plurality of scents having an observed capacity to suppress the individual's appetite. For example, the practitioner may determine, for each scent among those tested, whether the measure of its capacity to suppress the individual's appetite exceeds a selected level. As a result, the practitioner may identify a plurality of scents having a measured capacity to suppress the individual's appetite.

In another embodiment, a practitioner may additionally determine if the effect of a particular scent is dependent on the time of day. For example, a particular scent may have a suppressive effect on an individual's appetite in the morning but not in the afternoon or evening. In another example, a particular scent may have an especially powerful effect on an individual's appetite around the individual's regular mealtimes, but not at other times.

At step 215, information relating to the plurality of scents and the individual's responses to the plurality of scents is stored. For example, information including an identification of each of the scents that are identified as having a capacity to suppress the individual's appetite, and data relating to the individual's response to each respective scent (including any measurements of the scent's effect on the individual's appetite, the duration of the effects, etc.) may be stored in a database.

FIG. 3A shows a database storing information relating to various scents and an individual's responses to the scents in accordance with an embodiment. Database 300 contains information obtained from tests of an individual's response to various scents. Database 300 comprises four columns 302, 304, 306, 308. Column 302 stores identifiers for various scents. In the illustrative embodiment, scents are identified by number ("1," "2," "3," . . . ); however, in other embodiments, other identifiers may be used. Column 304 includes information indicating a quantity of the scent that was delivered in the test. Column 306 indicates a measure of the observed effect of the respective scent on the individual's appetite. In the illustrative embodiment, a negative percentage figure indicates suppression of appetite, a positive percentage indicates enhancement of appetite, while a zero value indicates no effect on appetite. Column 308 indicates the observed duration of the effect.

Thus, for example, referring to row 311, when the scent identified as scent 1 was delivered to the individual in quantity Q-1, the scent suppressed the individual's appetite by 60%. The effect lasted for 120 minutes. Referring to row 313, the scent identified as scent 2 was delivered in quantity Q-2; however, the scent had no observed effect on the individual's appetite. Referring to rows 315, 317, and 319, scent 3 enhances the individual's appetite, while scents 4 and 5 both suppress the individual's appetite. Database 300 may be stored, for example, in a computer or data storage device.

In various embodiments, database 300 may include data relating to one individual's responses to various scents, or may include data relating to multiple individuals' responses to various scents. While in the illustrative embodiment, a database is used to store data relating scents and data relating to an individual's response to scents, in other embodiments, other methods and other data structures may be used to store data.

Returning to the routine, at step 220, a schedule for delivering the plurality of scents is determined based on the information. For example, a schedule requiring delivery of the plurality of scents in a sequence, at time intervals determined based on the measured durations of the effects of the respective scents, may be generated.

A scent delivery schedule may be created based on any one or more of a variety of factors. In one embodiment, a scent delivery schedule may be created based on the time of day and the user's regular schedule of mealtimes. For example, a scent delivery schedule may indicate that a scent that has a strong suppressive effect on the individual's appetite may be delivered between 8:00 AM and 9:00 AM (when the individual normally eats breakfast), between 1:00 PM and 2:00 PM (when the individual normally eats lunch), and between 7:00 PM and 8:00 PM (when the individual normally eats dinner). The schedule may further specify that scents having a weak suppressive effect on the individual's appetite should be delivered at selected times between meals. Scent delivery schedules may be created based on other factors.

FIG. 3B shows an example of a scent delivery schedule that may be generated in accordance with an embodiment. In the illustrative embodiment, scent delivery schedule 390 is generated based on the data in database 300. Scent delivery schedule 390 comprises three columns 391, 392, 393. Column 391 contains scent identifiers associated with various scents that were found to suppress the individual's appetite. Column 392 indicates a quantity of the respective scent to be delivered. Column 393 indicates a duration associated with the respective scent. Thus, for example, row 396 indicates that scent 1 is to be delivered in the quantity Q-1, and that the effect is expected to last for 120 minutes. Row 397 indicates that scent 4 is to be delivered in the quantity Q-4, and that the effect is expected to last for 45 minutes. Row 398 indicates that scent 5 is to be delivered in the quantity Q-5, and that the effect is expected to last for 30 minutes. Schedule 390 may include other scents in addition to those shown in FIG. 3B. FIG. 3B is illustrative only. A scent delivery schedule may have a different form or structure than that shown in FIG. 3B, and may contain different types of information than that shown in FIG. 3B.

Referring again to FIG. 2, at step 225, the plurality of scents are delivered in accordance with the schedule. After the schedule for delivery of plurality of scents is generated, the plurality of scents are delivered to the individual in accordance with the schedule.

Thus, in the illustrative embodiment, a plurality of scents may be delivered as a sequence, based on scent delivery schedule 390, as follows. Scent 1 is delivered at a start time T in the quantity Q-1. 120 minutes later, scent 4 is delivered in the quantity Q-4. Scent 5 is delivered 45 minutes later in the quantity Q-5. Another scent may be delivered 30 minutes later. In one embodiment, the sequence of scents may be repeated indefinitely.

Scents may be delivered using any suitable scent delivery system or device. For example, the individual may wear a device that delivers scents to the nose. Alternatively, the individual may install a scent delivery device or system in one or more rooms of his or her home or office. Other scent delivery strategies and apparatus may be used.

Scent delivery systems and devices suitable for use in the present invention are taught in U.S. Pat. Nos. 6,803,987; 7,203,417; 7,036,502; and 7,376,344. These devices provide scent to a person and have the ability to provide multiple scents both simultaneously and sequentially. The contents of these U.S. Patents are incorporated herein by reference.

For example, as described in U.S. Pat. No. 6,803,987, a scent delivery device comprises a case and a fan for moving scent-laden air, the fan being housed in the case. The scent delivery device also includes one or more fragrance containers housed in the case, each of the fragrance containers having an inlet valve and an outlet valve, said inlet valve connected by an inlet tubing to the fan. The scent delivery device further comprises a mixing bed housed in the case, the mixed bed having an inlet connected to the outlet valve of each of the fragrance containers by an outlet tubing and having an outlet connected to nasal tubing. The scent delivery device also includes a scent delivery mechanism to be worn by a user at the user's nose so as to deliver scent directly to the user's nose and to remove scent from the user's nose, the delivery mechanism having an inlet connected to the nasal tubing and an outlet connected to exhaust tubing, and an electrical source housed in the case, the electrical source providing electricity to the fan so that the fan can move scent-laden air. The scent delivery mechanisms may be a nose mask, a face mask, or a T-joint, for example.

Figure 4:
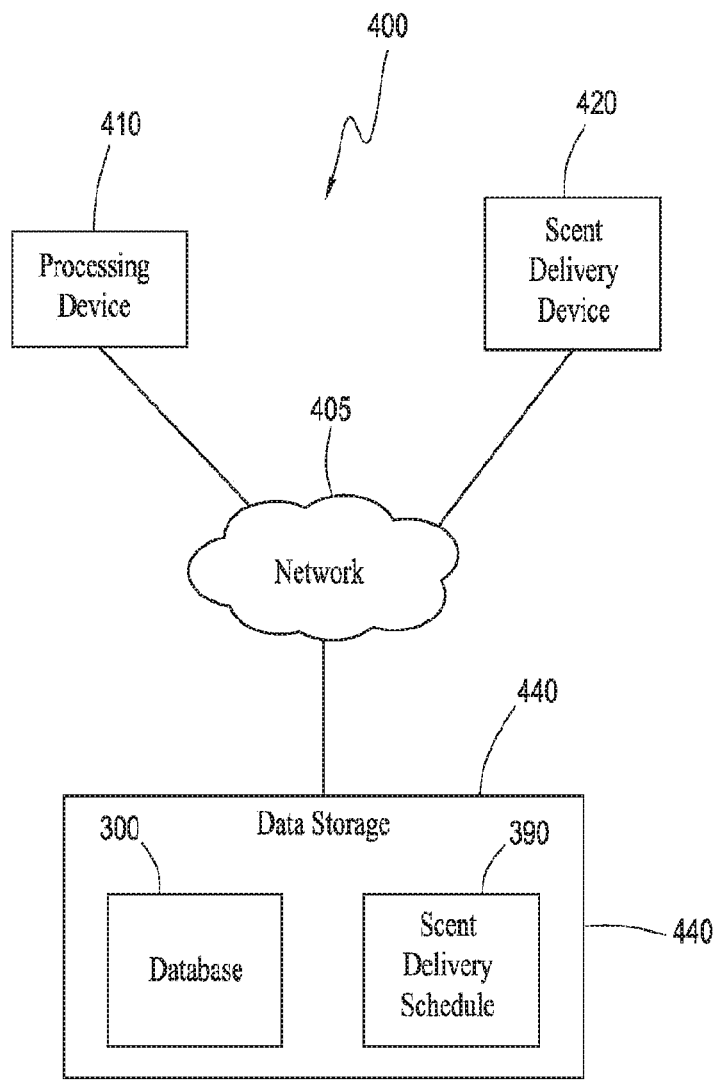
FIG. 4 shows components of a scent delivery system in accordance with an embodiment.

In accordance with another embodiment, some or all of the functions described above with reference to FIG. 1 and FIG. 2 may be performed by a system or device. FIG. 4 shows components of a scent delivery system that may be used to implement certain embodiments. Scent delivery system 400 comprises a processing device 410, a scent delivery device 420, a network 405, and a data storage 440.

Processing device 410 orchestrates the operation of various components of scent delivery system 400. For example, processing device 410 may from time to time instruct scent delivery device 420 to deliver a specified scent to an individual at a specified time. Processing device 410 may comprise a computer, for example.

Scent delivery device 420 delivers one or more scents to a user in response to control signals. Scent delivery device 420 may also be configured to generate a desired scent, as necessary. Scent delivery device 420 may include a storage adapted to store scent components (i.e., one or more chemicals and other substances that are used by scent delivery device 420 to generate and deliver a scent).

For example, scent delivery device 420 may be implemented using one or more of the devices and systems described in U.S. Pat. Nos. 6,803,987; 7,203,417; 7,036, 602; and 7,376,344, which are discussed above. These devices provide scent to a person and have the ability to provide multiple scents both simultaneously and sequentially.

Data storage 440 stores various types of data. In the illustrative embodiment, database 300 (shown in FIG. 3A) is stored in data storage 440. Similarly, scent delivery schedule 390 (shown in FIG. 3B) is stored in data storage 440. Data storage 440 may comprise any device or system capable of storing data, such as a personal computer, server computer, a storage device, etc.

Network 405 may comprise one or more of a number of different types of networks, such as, for example, the Internet, a Fibre Channel-based storage area network (SAN), an iSCSI-based network, a local area network (LAN), a wide area network (WAN), a wireless network, etc. Other networks may be used.

A practitioner may employ scent delivery system 400 to perform one or more of the actions described in the illustrative embodiment. For example, processing device 410 of scent delivery system 400 may be operated under the supervision of the practitioner to gather data relating to the effects of various scents on an individual's appetite. Specifically, processing device 410 may be configured to test the effectiveness of a first plurality of scents by delivering each scent to an individual and collecting data relating to the individual's responses to the scent (i.e., whether or not the scent influences the individual's appetite). The collected data may be stored in database 300. Database 300 may be stored in data storage 440, as shown in FIG. 4.

Scent delivery system 400 may be further configured to select, from among the first plurality of scents, a second plurality of scents that have a desired effect on the individual's appetite, based on the stored data. For example, processing device 410 may examine the data in database 300 and select a second plurality of scents that have an observed effect of suppressing the individual's appetite. Processing device 410 may also be configured to generate a scent delivery schedule such as schedule 390 (shown in FIG. 3B) to be used to deliver scents to the individual in order to achieve a desired purpose, such as suppressing the individual's appetite. The scent delivery schedule 390 may also be stored in data storage 440, as shown in FIG. 4.

Subsequently, scent delivery system 400 may be used to deliver the second plurality of scents to the individual according to the defined schedule. Thus, processor 410 may examine scent delivery schedule 390, and (possibly with input from a practitioner) instruct or otherwise cause scent delivery device 420 to generate (as necessary), and deliver, the scents indicated in the schedule, in accordance with scent delivery schedule 390.

Figure 5:
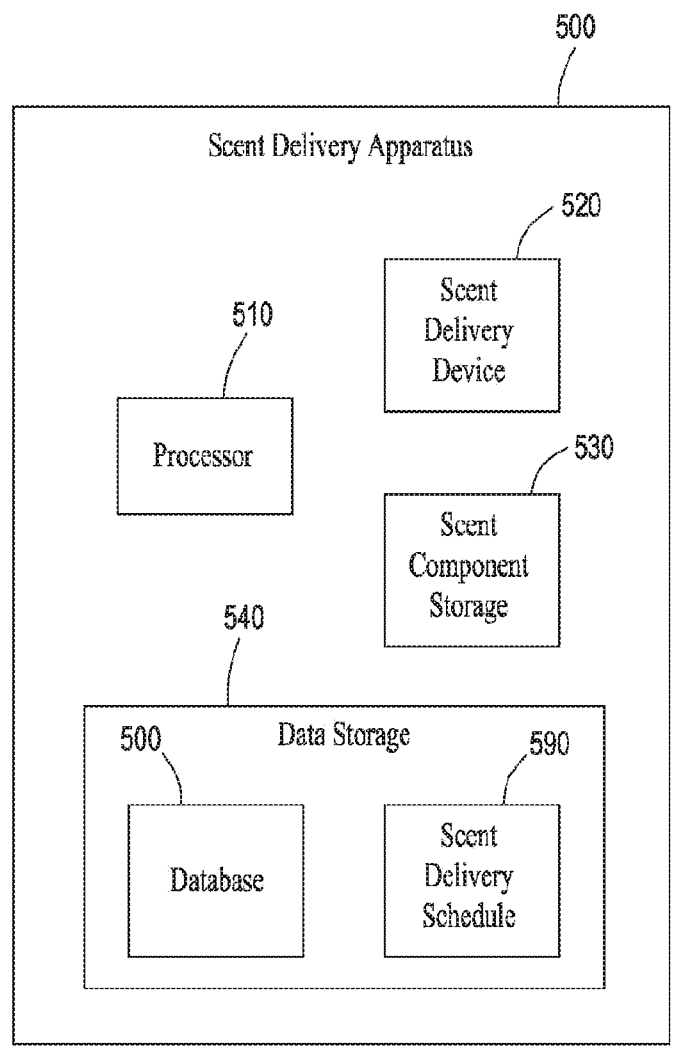
FIG. 5 shows components of a scent delivery apparatus in accordance with an embodiment.

In accordance with another embodiment illustrated in FIG. 5, a scent delivery apparatus is provided. Scent delivery apparatus 500 may be employed by a user at home, for example. Scent delivery apparatus 500 comprises a processor 510, a scent delivery device 520, a scent component storage 530, and a data storage 540.

Processor 510 orchestrates the operation of other components of scent delivery apparatus 500. Scent delivery device 520 delivers one or more selected scents in response to control signals. Scent delivery device 520 may also generate a desired scent as necessary. Scent component storage 530 stores chemicals and other components that may be used by scent delivery device 520 to generate a desired scent. Data storage 540 stores various types of data.

In an illustrative embodiment, an individual may maintain scent delivery apparatus 500 in a room of his or her home. Suppose, for example, that an individual wishes to employ scent delivery apparatus 500 to suppress his appetite for chocolate. The individual may place scent delivery apparatus 500 in a room of his home, such as the kitchen, where it will be conveniently accessible.

Scent delivery apparatus 500 may include computer software configured to deliver a first plurality of scents to the individual, and receive information indicating the individual's appetite response to each scent. For example, processor 510 may execute an initialization program in which various scents are delivered to the individual. As each scent is delivered, processor 510 presents to the individual, via a display screen (or via automated voice messaging technology) a series of questions concerning the effect of the scent on the individual's appetite. In the illustrative embodiment, processor 510 may ask the individual whether the scent decreases or increases his appetite for chocolate, and by how much. In response to the questions, the individual may indicate his or her answer, including whether or not the scent influenced his or her appetite. The individual may submit answers to the questions using a keyboard and display screen, by voice command, or by other suitable means. Processor 510 may analyze the individual's answers and generate data relating to the effect of various scents on the individual's appetite for chocolate. Processor 510 may store such data in a database, such as database 500 shown in FIG. 5. Processor 510 may subsequently generate a scent delivery schedule 590 specifying a plurality of scents to be delivered, and a delivery schedule, based on the data obtained. Scent delivery schedule 590 is stored in data storage 540.

After a scent delivery schedule is generated and stored, processor 510 may cause scent delivery device 520 to deliver the specified scents based on the scent delivery schedule. Scent delivery device 520 may comprise a component that must be worn by the individual. For example, scent delivery device 520 may include a scent delivery mechanism to be worn by a user at the user's nose.

In other embodiments, measurements of the effects of various scents on a plurality of individuals may be stored in a database. This data may be used to assist in identifying scents having a higher probability of having a desired effect (e.g., suppressing an individual's appetite).

In various embodiments, the method steps described herein, including the method steps described in FIGS. 1 and/or 2, may be performed in an order different from the particular order described or shown. In other embodiments, other steps may be provided, or steps may be eliminated, from the described methods.

Systems, apparatus, and methods described herein may be implemented using digital circuitry, or using one or more computers using well-known computer processors, memory units, storage devices, computer software, and other components. Typically, a computer includes a processor for executing instructions and one or more memories for storing instructions and data. A computer may also include, or be coupled to, one or more mass storage devices, such as one or more magnetic disks, internal hard disks and removable disks, magneto-optical disks, optical disks, etc.

Systems, apparatus, and methods described herein may be implemented using computers operating in a client-server relationship. Typically, in such a system, the client computers are located remotely from the server computer and interact via a network. The client-server relationship may be defined and controlled by computer programs running on the respective client and server computers.

Systems, apparatus, and methods described herein may be used within a network-based cloud computing system. In such a network-based cloud computing system, a server or another processor that is connected to a network communicates with one or more client computers via a network. A client computer may communicate with the server via a network browser application residing and operating on the client computer, for example. A client computer may store data on the server and access the data via the network. A client computer may transmit requests for data, or requests for online services, to the server via the network. The server may perform requested services and provide data to the client computer(s). The server may also transmit data adapted to cause a client computer to perform a specified function, e.g., to perform a calculation, to display specified data on a screen, etc.

Systems, apparatus, and methods described herein may be implemented using a computer program product tangibly embodied in an information carrier, e.g., in a non-transitory machine-readable storage device, for execution by a programmable processor; and the method steps described herein, including one or more of the steps of FIGS. 1 and/or 2, may be implemented using one or more computer programs that are executable by such a processor. A computer program is a set of computer program instructions that can be used, directly or indirectly, in a computer to perform a certain activity or bring about a certain result. A computer program can be written in any form of programming language, including compiled or interpreted languages, and it can be deployed in any form, including as a stand-alone program or as a module, component, subroutine, or other unit suitable for use in a computing environment.

Figure 6:
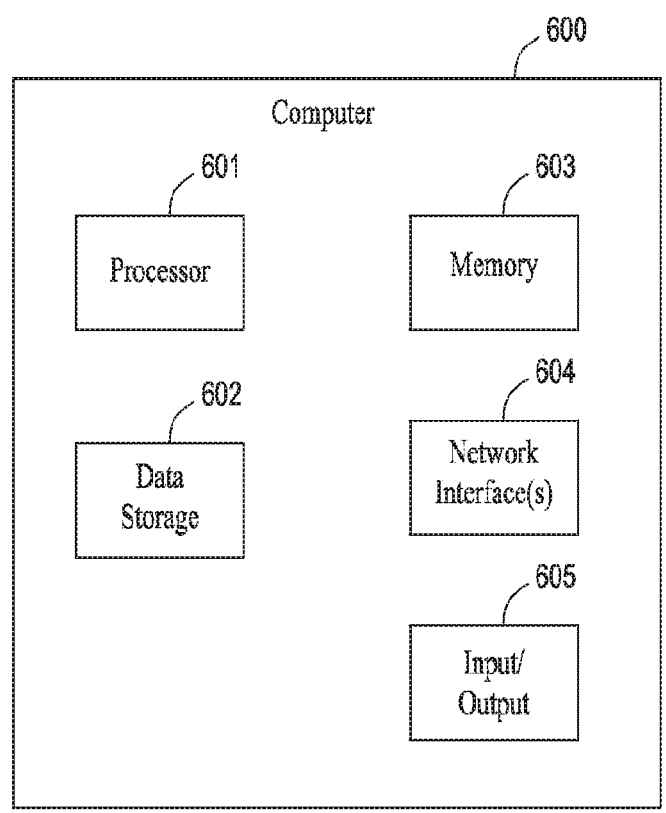
FIG. 6 shows components of an exemplary computer that may be used to implement certain embodiments.

A high-level block diagram of an exemplary computer that may be used to implement systems, apparatus and methods described herein is illustrated in FIG. 6. Computer 600 includes a processor 601 operatively coupled to a data storage device 602 and a memory 603. Processor 601 controls the overall operation of computer 600 by executing computer program instructions that define such operations. The computer program instructions may be stored in data storage device 602, or other computer readable medium, and loaded into memory 603 when execution of the computer program instructions is desired. Thus, the method steps of FIGS. 1 and/or 2 can be defined by the computer program instructions stored in memory 603 and/or data storage device 602 and controlled by the processor 601 executing the computer program instructions. For example, the computer program instructions can be implemented as computer executable code programmed by one skilled in the art to perform an algorithm defined by the method steps of FIGS. 1 and/or 2. Accordingly, by executing the computer program instructions, the processor 601 executes an algorithm defined by the method steps of FIGS. 1 and/or 2. Computer 600 also includes one or more network interfaces 604 for communicating with other devices via a network. Computer 600 also includes one or more input/output devices 605 that enable user interaction with computer 600 (e.g., display, keyboard, mouse, speakers, buttons, etc.).

Processor 601 may include both general and special purpose microprocessors, and may be the sole processor or one of multiple processors of computer 600. Processor 601 may include one or more central processing units (CPUs), for example. Processor 601, data storage device 602, and/or memory 603 may include, be supplemented by, or incorporated in, one or more application-specific integrated circuits (ASICs) and/or one or more field programmable gate arrays (FPGAs).

Data storage device 602 and memory 603 each include a tangible non-transitory computer readable storage medium. Data storage device 602, and memory 603, may each include high-speed random access memory, such as dynamic random access memory (DRAM), static random access memory (SRAM), double data rate synchronous dynamic random access memory (DDR RAM), or other random access solid state memory devices, and may include non-volatile memory, such as one or more magnetic disk storage devices such as internal hard disks and removable disks, magneto-optical disk storage devices, optical disk storage devices, flash memory devices, semiconductor memory devices, such as erasable programmable read-only memory (EPROM), electrically erasable programmable read-only memory (EEPROM), compact disc read-only memory (CD-ROM), digital versatile disc read-only memory (DVD-ROM) disks, or other non-volatile solid state storage devices.

Input/output devices 605 may include peripherals, such as a printer, scanner, display screen, etc. For example, input/output devices 605 may include a display device such as a cathode ray tube (CRT) or liquid crystal display (LCD) monitor for displaying information to the user, a keyboard, and a pointing device such as a mouse or a trackball by which the user can provide input to computer 600.

Any or all of the systems and apparatus discussed herein, including processing device 410, data storage 440, processor 510, data storage 540, and components thereof, may be implemented using a computer such as computer 600.

One skilled in the art will recognize that an implementation of an actual computer or computer system may have other structures and may contain other components as well, and that FIG. 6 is a high level representation of some of the components of such a computer for illustrative purposes.

In accordance with another embodiment, a scent delivery system monitors a user's consumption of food over time while the user is exposed to a particular scent, generates consumption data representing the user's consumption of food over time while the user is exposed to the scent, and determines a measure of a scent's effectiveness on the user's consumption of food (and/or a measure of the scent's effectiveness on the user's appetite) based on the consumption data. One or more scents may be examined to determine the user's response to each scent. Data indicating each scent's effectiveness, the time required for the scent to take effect, the duration of the scent's effectiveness, etc., may be generated and stored. A scent delivery schedule may be generated based on the stored data, and a plurality of scents may be selected and delivered to the user based on the scent delivery schedule.

Figure 7:
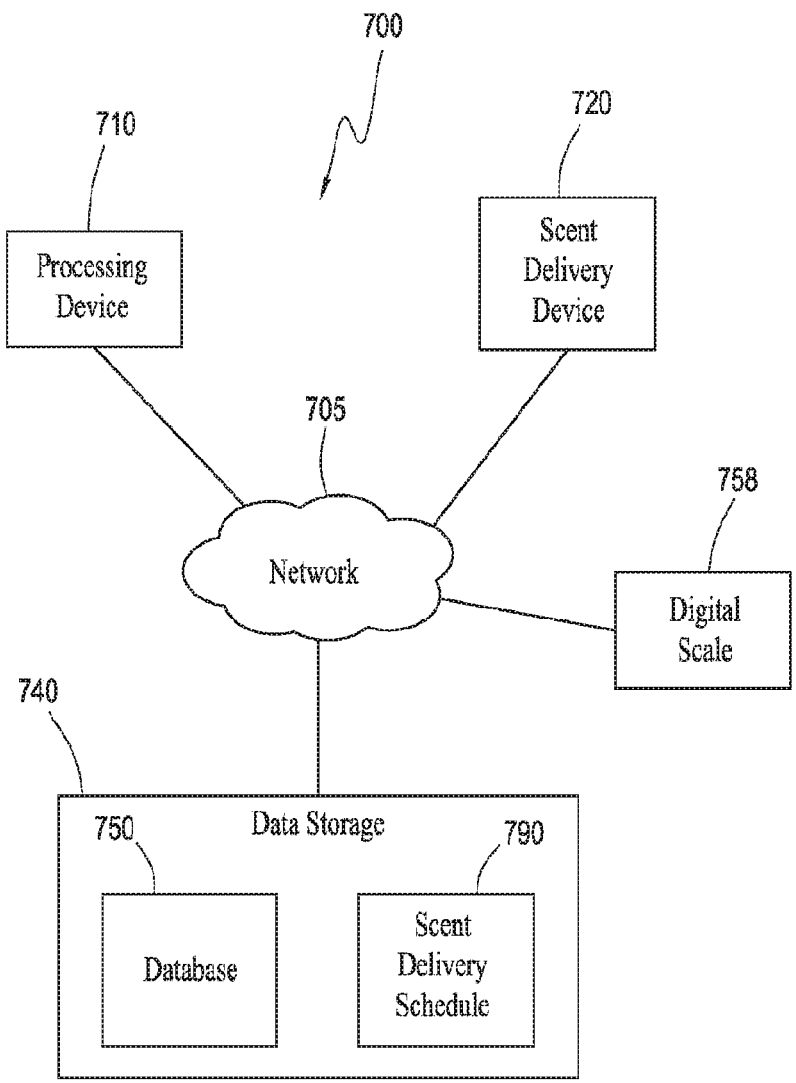
FIG. 7 shows components of a scent delivery system in accordance with another embodiment.

FIG. 7 shows components of a scent delivery system in accordance with an embodiment. Scent delivery system 700 includes components similar to components shown in FIG. 4. Thus, scent delivery system 700 includes a processing device 710, a scent delivery device 720, a network 705, and a data storage 740.

Processing device 710 is similar to processing device 410 of FIG. 4 and orchestrates the operation of various components of scent delivery system 700. Processing device 710 may comprise a computer, for example. Scent delivery device 720 is similar to scent delivery device 420 of FIG. 4 and delivers one or more scents to a user in response to control signals. Data storage 740 stores various types of data. In the illustrative embodiment, a database 750 is stored in data storage 740. Similarly, a scent delivery schedule 790 is stored in data storage 740. Data storage 740 may comprise any device or system capable of storing data, such as a personal computer, server computer, a storage device, etc.

Network 705 may comprise one or more of a number of different types of networks, such as, for example, the Internet, a Fibre Channel-based storage area network (SAN), an iSCSI-based network, a local area network (LAN), a wide area network (WAN), a wireless network, etc. Other networks may be used.

Figure 8:
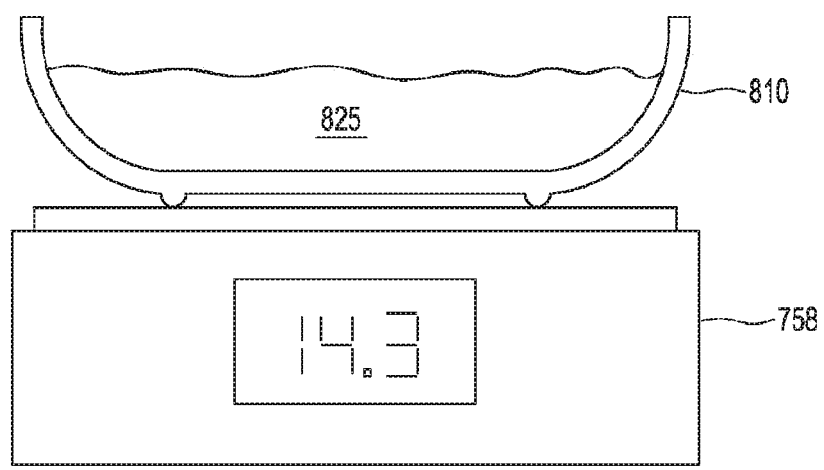
FIG. 8 shows a digital scale in accordance with an embodiment.

Scent delivery system 700 also includes a digital scale 758. Digital scale 758 may be any commercially available digital scale having sufficient sensitivity to detect a change in the mass of the food in a typical meal as a user consumes the food, for example. FIG. 8 shows digital scale 758 in accordance with an embodiment. A dish 810 holding a quantity of a food 825 rests on scale 758. Digital scale 758 measures the weight (or mass) of dish 810 and food 825 and transmits weight data (or mass data) to processing device 710. The weight or mass of food 825 alone may be derived from measurements taken by digital scale 758.

In one embodiment, scent delivery system 700 is used to measure the effect of a scent on a user's consumption of food. Specifically, a meal is placed on digital scale 758, and a user consumes the meal while the food is on the scale. Also, while the user is consuming the food, scent delivery device 720 delivers a scent to the user. Processing device 710 monitors the weight/mass of the food being consumed while the user is exposed to the scent. Processing device 710 may then generate a consumption curve showing a relationship between the weight/mass of the food and time.

Figure 9:
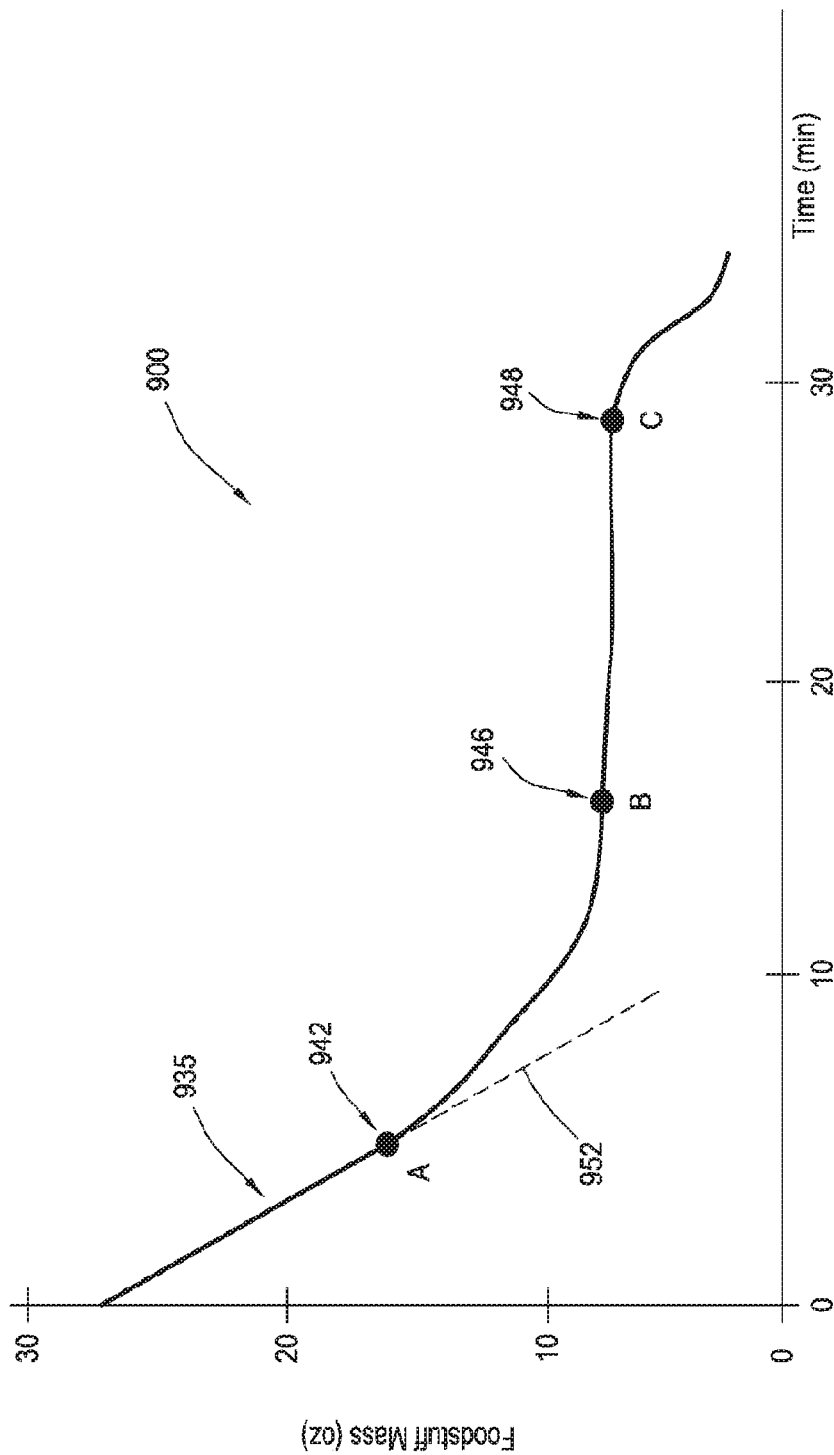
FIG. 9 shows a consumption curve in accordance with an embodiment.

FIG. 9 shows a graph 900 showing an example of a consumption curve 935, which shows a relationship between the weight/mass of food being consumed by a user and time, in accordance with an embodiment. In particular, the mass of food (measured in ounces) being consumed by a user is measured over time (measured in minutes) while the user is exposed to a particular scent. FIG. 9 is illustrative only.

In one embodiment, processing device 710 may obtain information concerning a particular scent by analyzing the user's rate of consumption, which is equal to the first derivate (also referred to as the slope) of the consumption curve associated with the particular scent. Processing device 710 may also obtain information concerning the particular scent by examining the second derivative of the consumption curve at various points. Referring to FIG. 9, for example, a first derivative (slope) of curve 935 at point A (942) is represented by dotted line 952. Processing device 710 may identify points where the first derivative is positive, points where the first derivative is negative (such as point A (942)), and points where the first derivative is zero or near zero (such as point B (946) and point C (948)). Processing device 710 may also analyze the second derivative of a consumption curve and identify points of interest where the second derivative is negative, positive, or zero, and/or has other characteristics.

In one embodiment, processing device 710 may use data concerning a consumption curve (including the first derivative thereof, the second derivative thereof, etc.) to determine information concerning a particular scent, including the effectiveness of the scent, the duration of the scent's effectiveness, how long it takes for the scent to take effect, etc. Based on such information, processing device 710 may generate a scent delivery schedule for an individual. For example, processing device 710 may generate a consumption curve showing the effect of a particular scent on an individual's consumption of food, identify a region of the curve where the first derivate is zero or near zero, conclude that the identified region represents a period of time when the individual has stopped eating, and determine that the scent has effectively suppressed the person's appetite during that period of time. Processing device 710 may further determine that a duration corresponding to the region represents a duration of the effectiveness of the particular scent on the person's consumption (and/or appetite).

Referring to FIG. 9, for example, processing device 710 may determine that the first derivative of curve 935 is zero (or near zero) in the region between point B (946) and point C (948). Processing device 710 may accordingly determine that this region of the curve represents a period of time when the user stopped eating because the scent being delivered had suppressed the user's appetite. In the illustrative embodiment of FIG. 9, processing device 710 further determines that the first derivative turns negative after point C (948), indicating that the user again began to consume food, and that therefore the scent's effectiveness ended at or around point C (948). Processing device 710 therefore determines the estimated duration of the scent's effectiveness to be equal to the time period represented by the region between point B (946) and point C (948).

Processing device 710 may examine the second derivative of a consumption curve to determine information concerning a particular scent. For examine, a consumption curve showing a greater second derivative in a particular region may indicate that a scent takes effect more rapidly, while a lower second derivative may indicate that the scent takes effect more slowly.

Processing device 710 may use methods and systems described above to generate and examine multiple consumption curves associated with different scents, and to construct a scent delivery schedule based on the consumption curve data. For example, after an estimated duration of a particular scent's effectiveness is determined based on a consumption curve associated with the scent, processing device 710 may include the scent in a scent delivery schedule for a period of time equal to the estimated duration of the scent's effectiveness. The scent delivery schedule may specify that after the estimated duration has elapsed, a different scent should be delivered.

Processing device 710 may also examine multiple consumption curves to compare the effectiveness of different scents. Processing device 710 may select a scent from among a plurality of available scents based on information obtained from the associated consumption curve.

The foregoing Detailed Description is to be understood as being in every respect illustrative and exemplary, but not restrictive, and the scope of the invention disclosed herein is not to be determined from the Detailed Description, but rather from the claims as interpreted according to the full breadth permitted by the patent laws. It is to be understood that the embodiments shown and described herein are only illustrative of the principles of the present invention and that various modifications may be implemented by those skilled in the art without departing from the scope and spirit of the invention. Those skilled in the art could implement various other feature combinations without departing from the scope and spirit of the invention.

The invention claimed is:

1. A method of delivering scents to influence an individual's appetite, the method comprising:
   delivering, by a scent delivery device, a first plurality of scents to an individual;
   determining, by a processor, for each respective scent among the first plurality of scents, an effect of the respective scent on an appetite of the individual and a first duration of the effect of the respective scent on the appetite of the individual, wherein determining a respective effect of a particular scent selected from among the first plurality of scents comprises:
   using a scale to generate measurements of a weight of a food over time as the individual consumes the food while exposed to the respective scent;
   determining, by the processor, a measurement of a relationship between a consumption of the food by the individual while the individual is exposed to the particular scent, and time, based on the measurements of the weight of the food; and determining, by the processor, a second duration of an effectiveness of the particular scent based on the relationship;

identifying, by the processor, a second plurality of scents that produce a particular effect on the appetite of the individual based on the effects, the first durations, and the second duration determined;

generating, by the processor, a delivery schedule for delivery of one or more of the second plurality of scents based on the effects, the first durations, the second duration, and a regular schedule of mealtimes of the individual; and delivering, by the scent delivery device, the one or more of the second plurality of scents in accordance with the delivery schedule to produce the particular effect on the appetite of the individual;

wherein the scent delivery device comprises:

a case;

a plurality of scent containers housed in the case;

a fan housed in the case for moving scented air from the plurality of scent containers to a nose of the user;

an electrical power source housed in the case for providing electricity to the fan; and a scent delivery mechanism worn by the user and positioned at the nose of the user to deliver the scented air to the nose of the user.

2. The method of claim 1, wherein the particular effect includes one of suppression of the appetite of the individual and enhancement of the appetite of the individual.

3. The method of claim 1, further comprising:

storing, in a memory, data relating to the responses of the individual to the first plurality of scents.

4. The method of claim 2, wherein the particular effect comprises suppression of the appetite of the individual;

the method further comprising:

determining, by the processor, for each one of the second plurality of scents, a measure of a capacity of the respective scent to suppress the appetite of the individual; and identifying, by the processor, the second plurality of scents based on the measured capacity of each respective scent to suppress the appetite of the individual.

* * * * *